_(12)_ United States Patent
Abraini

US008435569B2

(10) Patent No.: US 8,435,569 B2
(45) Date of Patent: May 7, 2013

(54) PHARMACEUTICAL COMPOSITION COMPRISING AT LEAST ONE THROMBOLYTIC AGENT (A) AND AT LEAST ONE GAS (B) SELECTED FROM THE GROUP CONSISTING OF NITROUS OXIDE, ARGON, XENON, HELIUM, NEON

(75) Inventor: Jacques H. Abraini, Caen (FR)

(73) Assignee: NNOXE Pharmaceutiques Inc., Quebec (CA)

( * ) Notice: Subject to any disclaimer, the term of this patent is extended or adjusted under 35 U.S.C. 154(b) by 394 days.

(21) Appl. No.: 12/598,225

(22) PCT Filed: Apr. 30, 2008

(86) PCT No.: PCT/EP2008/055392
§ 371 (c)(1),
(2), (4) Date: May 6, 2010

(87) PCT Pub. No.: WO2008/132239
PCT Pub. Date: Nov. 6, 2008

(65) Prior Publication Data
US 2010/0278942 A1 Nov. 4, 2010

Related U.S. Application Data

(60) Provisional application No. 60/914,896, filed on Apr. 30, 2007.

(30) Foreign Application Priority Data

Apr. 30, 2007 (EP) ..................................... 07107219

(51) Int. Cl.
*A01N 59/00* (2006.01)
*A61K 33/00* (2006.01)
(52) U.S. Cl.
USPC ........................... 424/718; 424/600; 424/94.1
(58) Field of Classification Search .................. None
See application file for complete search history.

(56) References Cited

U.S. PATENT DOCUMENTS

| | | | |
|---|---|---|---|
| 6,274,633 B1 | 8/2001 | Franks et al. | |
| 6,559,190 B1 | 5/2003 | Petzelt et al. | |
| 6,653,354 B2 | 11/2003 | Franks et al. | |
| 2004/0258766 A1 * | 12/2004 | Lemaire .................. | 424/600 |
| 2005/0152988 A1 | 7/2005 | Lemaire et al. | |
| 2005/0244508 A1 | 11/2005 | Neu et al. | |
| 2007/0275089 A1 | 11/2007 | Lemaire et al. | |

FOREIGN PATENT DOCUMENTS

| | | |
|---|---|---|
| EP | 1 158 992 B1 | 9/2003 |
| EP | 1 552 840 A1 | 7/2005 |
| FR | 2 863 169 A1 | 6/2005 |
| WO | WO 99/20251 A1 | 4/1999 |
| WO | WO 01/08692 A1 | 2/2001 |
| WO | WO 03/047603 A2 | 6/2003 |

OTHER PUBLICATIONS

Gold et al. "Acute coronary reocclusion after thrombolysis with recombinant human tissue-type plasminogen activator: prevention by a maintenance infusion" Circulation, 1986, vol. 73, pp. 347-352.*
Asahi et al., "Reduction of Tissue Plasminogen Activator-Induced Hemorrhage and Brain Injury by Free Radical Spin Trapping After Embolic Focal Cerebral Ischemia in Rats," J. Cereb. Blood Flow Metab., 2000, p. 452, vol. 20.
Binda et al., "Note Therapeutique—Place Des Medicaments Thrombolytiques Dans—Le Traitement De La Malaria Cerebrale—," Med. Afrique Noire, 1990, pp. 214-215, vol. 37, No. 4. oi et al., "Pharmacology of Glutamate Neurotoxicity in Cortical Cell Culture: Attenuation by NMDA Antagonists," J. Neurosci., 1988, pp. 185-196, vol. 8, No. 1.
David et al., "Nitrous Oxide and Xenon Prevent Amphetamine-Induced Carrier-Mediated Dopamine Release in a Memantine-Like Fashion and Protect Against Behavioral Sensitization," Biol. Psychiatry, 2006, pp. 49-57, vol. 60.
David et al., "Neuroprotective effects of xenon: a therapeutic window of opportunity in rats subjected to transient cerebral ischemia," FASEB J., 2008, pp. 1275-1286, vol. 22.
David et al., "Reduction of Ischemic Brain Damage by Nitrous Oxide and Xenon," J. Cereb. Blood Flow Metab., 2003, pp. 1168-1173, vol. 23, No. 10.
Davis et al., "Selfotel in Acute Ischemic Stroke—Possible Neurotoxic Effects of an NMDA Antagonist," Stroke, 2000, p. 347-354, vol. 31.
Dirnagl et al., Pathobiology of ischaemic stroke: an integrated view, Trends Neurosci., 1999, pp. 391-397, vol. 22, No. 9.
Franks et al., "How does xenon produce anaesthesia?" Nature, 1998, p. 324, vol. 396.
Goldberg et al., "Combined Oxygen and Glucose Deprivation in Cortical Cell Culture: Calcium-dependent and Calcium-independent Mechanisms of Neuronal Injury," J. Neurosci., 1993, pp. 3510-3523, vol. 13, No. 8.
Goto et al., "The blood-gas partition coefficient of Xenon may be lower than generally accepted," Br. J. Anaesth, 1998, pp. 255-256, vol. 80.
Guillausseau and Dupuy, "Antithrombotiques et diabète," Arch. Mal. Coeur Vaiss., 1996, pp. 1557-1560, vol. 89, No. 11.
Haelewyn et al., "Neuroprotection by nitrous oxide: Facts and evidence," Crit. Care Med., 2008, pp. 2651-2659, vol. 36, No. 9.
Hobbs et al., "Xenon and Hypothermia Combine Additively, Offering Long-Term Function and Histopathologic Neuroprotection After Neonatal Hypoxia/Ischemia," Stroke, 2008, pp. 1307-1313, vol. 39.

(Continued)

*Primary Examiner* — James H Alstrum Acevedo
*Assistant Examiner* — Daniel L Branson
(74) *Attorney, Agent, or Firm* — Foley & Lardner LLP

(57) ABSTRACT

The present invention relates to a pharmaceutical composition comprising at least one thrombolytic agent (A), such as the human recombinant form of tissue-type plasminogen activator (rt-PA), and at least one gas (B) selected from the group consisting of nitrous oxide, argon, xenon, helium, neon, and mixtures thereof, as a combined composition for simultaneous, separate or sequential use for treating ischemia. The present invention also relates to the use of at least one thrombolytic agent (A), such as the human recombinant form of tissue-type plasminogen activator (rt-PA), and at least one gas (B) selected from the group consisting of nitrous oxide, argon, xenon, helium, neon, and mixtures thereof, for the preparation of a combined pharmaceutical composition for treating ischemia.

17 Claims, 5 Drawing Sheets

OTHER PUBLICATIONS

Homi et al., "The Neuroprotective Effect of Xenon Administration during Transient Middle Cerebral Artery Occlusion in Mice," Anesthesiology, 2003, pp. 876-881, vol. 99, No. 4.

Jevtovic et al., "Nitrous oxide (laughing gas) is an NMDA antagonist, neuroprotectant and neurotoxin," Nature Med., 1998, pp. 460-463, vol. 4, No. 4.

Kaur et al., "Review Article—The Neurotoxicity of Tissue Plasminogen Activator?"J. Cereb. Blood Flow Metab., 2004, pp. 945-963, vol. 24, No. 9.

Ma et al., "Xenon and Hypothermia Combine to Provide Neuroprotection from Neonatal Asphyxia," Ann. Neurol., 2005, pp. 182-193, vol. 58, No. 2.

Martin et al., "Asynchronous administration of xenon and hypothermia significantly reduces brain infarction in the neonatal rat," Br. J. Anaesth., 2007, pp. 236-240, vol. 98, No. 2.

Meyer J S et al., "Why emergency XeCT-CBF should become routine in acute ischemic stroke before thrombolytic therapy," XP009104218, 2008, pp. A25-A28, vo. 14, No. 56:53.

Nighoghossain et al., "Hyperbaric oxygen in the treatment of acute ischemic stroke," Stroke, XP-002445414, 1995, pp. 1396-1372, vol. 26.

Ohsawa et al., "Hydrogen acts as a therapeutic antioxidant by selectively reducing cytotoxic oxygen radicals," Nature Med., 2007, pp. 688-694, vol. 13, No. 6.

Olney et al., "Pathological Changes Induced in Cerebrocortical Neurons by Phencyclidine and Related Drugs," Science, 1989, pp. 1360-1362, vol. 244.

Olney et al., "NMDA Antagonist Neurotoxicity: Mechanism and Prevention," Science, 1991, pp. 1515-1518, vol. 254.

Pagel et al., "Noble Gases Without Anesthetic Properties Protect Myocardium Against Infarction by Activating Prosurvival Signaling Kinases and Inhibiting Mitochondrial Permeability Transition In Vivo," Anesth Analg., 2007, pp. 562-569, vol. 105, No. 3.

Pan et al., "Heliox and oxygen reduce infarct volume in a rat model of focal ischemia," Exp Neurol., 2007, pp. 587-590, vol. 205.

Parsons et al., "Glutamate in CNS Disorders as a Target for Drug Development: An Update," Drug News Perspect., 1998, pp. 523-569, vol. 11, No. 9.

Rajakumaraswamy et al.,"Neuroprotective interaction produced by xenon and dexmedetomidine on in vitro and in vivo neuronal injury models," Neurosci. Lett., 2006, p. 128, vol. 409.

Rubiera et al., "Predictors of Early Arterial Reocclusion After Tissue Plasminogen Activator-Induced Recanalization in Acute Ischemic Stroke," Stroke, 2005, pp. 1452-1456, vol. 36.

Sattler et al., "Distinct Influx Pathways, Not Calcium Load, Determine Neuronal Vulnerability to Calcium Neurotoxicity," J. Neurochem., 1998, pp. 2349-2364, vol. 71, No. 6.

Smith, "Therapeutic N-methyl-D-aspartate receptor antagonists: Will reality meet expectation?" Curro Opin. Investig. Drugs, 2003, pp. 826-832, vol. 4, No. 7.

Merck Res. Lab, "Treatment of ischemic stroke," The Merck Index, 1999, Chapter 174, pp. 1421-1423.

Tsirka et al., "Excitotoxin-Induced neuronal degeneration and seizure are mediated by tissue plasminogen activator," Nature, 1995, pp. 340-344, vol. 377.

Wang et al., "Tissue plasminogen activator (tPA) increases neuronal damage after focal cerebral ischemia in wild-type and tPA-deficient mice," Nature Med., 1998, pp. 228-231, vol. 4, No. 2.

Yamakura et al., "Effects of Gaseous Anesthetics Nitrous Oxide and Xenon on Ligand-gated Ion Channels," Anesthesiology, 2000, pp. 1095-1101, vol. 93, No. 4.

Yanaka et al., "Current and Future Therapies for Ischemic Cerebrovascular Disease," Drugs Today, 2000, pp. 807-815, vol. 36, No. 12.

Yarin et al., "Argon protects hypoxia-, cisplatin- and gentamycin-exposed hair cells in the newborn rat's organ of Corti," Hear Res., 2005, pp. 1-9, vol. 201.

Zweifler, "Management of Acute Stroke" Southern Medical Journal, XP009087512, 2003, pp. 380-385, vol. 96, No. 4.

European Search Report issued in application No. EP 07107219 on Aug. 6, 2007.

International Search Report issued in application No. PCT/EP2008/055392 on Aug. 20, 2008.

* cited by examiner

•P < 0.05 vs Air; + P < 0.05 vs Air + t-PA. N = 3, n = 9-16 per condition

*P < 0.05, n = 8 per condition

PHARMACEUTICAL COMPOSITION COMPRISING AT LEAST ONE THROMBOLYTIC AGENT (A) AND AT LEAST ONE GAS (B) SELECTED FROM THE GROUP CONSISTING OF NITROUS OXIDE, ARGON, XENON, HELIUM, NEON

The present invention generally relates to a method for treating ischemia comprising administering to a patient in need thereof at least one gas selected from the group consisting of nitrous oxide, xenon, argon, helium, neon, and mixtures thereof.

In particular, the present invention relates to a pharmaceutical composition comprising: (i) at least one thrombolytic drug such as, but not limited to, streptokinase, urokinase, alteplase (human recombinant tissue-type plasminogen activator or rt-PA), reteplase or tenecteplase, which are serine proteases derived either from Streptomyces or recombinant technology, and (ii) at least one gas or a mixture of gases selected from the group consisting of nitrous oxide, xenon, argon, helium, and neon, as a combined composition for simultaneous, separate or sequential use for treating ischemic insults such as, but not limited to, cerebral ischemia, cardiac ischemia, renal ischemia, retinal ischemia, or lower limb's ischemia.

The present invention also relates to the use of at least one thrombolytic agent (A), such as the human recombinant form of tissue-type plasminogen activator (rt-PA), and at least one gas (B) selected from the group consisting of nitrous oxide, argon, xenon, helium, neon, and mixtures thereof, for the preparation of a combined pharmaceutical composition for treating ischemia.

Ischemia is a restriction in blood supply generally due to factors in the blood vessels, particularly thromboembolism (blood clots), which lead to tissue dysfunction and cell death through necrotic and apoptotic mechanisms. Ischemia is an absolute or relative shortage of the blood supply to an organ. Relative shortage means the mismatch of blood supply and blood request for adequate oxygen (and glucose) delivery in tissue. The extent of tissue damage mainly depends on the level and duration of ischemia. The heart, the kidneys, and the brain are among the organs that are the most sensitive to inadequate blood supply. For instance, ischemic stroke (also called brain attack or acute cerebral ischemia) and myocardial infarction (also called heart attack or acute cardiac ischemia) are with cancer the major causes of death in humans. It is estimated that global cardiovascular deaths will increase from 17 million deaths to more than 23 million deaths in 2030, and that cerebral stroke will represent more than 6% of the diseases' global impact in 2020-2025 with nearly 25% of males and 20% of females who will suffer a brain attack before reaching 85-year old.

Proteolysis is a general catalytic physiological process, which can be defined as the directed (oriented) degradation of proteins by cellular enzymes called proteases. Fibrinolysis is a specific case of proteolysis. Fibrinolysis is the physiological process wherein a fibrin clot, the product of coagulation, is broken down. In the case of vascular injury, such as the production of blood (fibrin) clot, endothelial cells release a serine protease called tissue-type plasminogen activator (t-PA) that converts the proenzyme plasminogen to plasmin, the main enzyme of fibrin, which cuts the fibrin mesh. In healthy subjects, this process allows avoiding excessive clot formation and ischemic accidents. In patients suffering thromboembolism and ischemia, fibrinolysis can be stimulated through administration of analogs of tissue-type plasminogen activator. This breakdown of blood clots by pharmacological means is called thrombolysis. Thrombolysis is the major therapeutic strategy for treating ischemic insults. For instance, today, the intravenous or intra-arterial injection of rt-PA is the only therapy approved by the Food and Drug Administration and the European Medical Agencies for treating ischemic stroke, i.e. acute cerebral ischemia. However, under certain conditions, thrombolytic therapy is associated with a risk of hemorrhagic transformation and neuronal death potentiation that is due to the general proteolytic properties of plasmin. In order to avoid such adverse side effects of plasmin, rt-PA has to be administered to the patient within an appropriate period, called "therapeutic window", typically of up to 3 hours, following the occurrence of the symptoms induced by ischemia according to the current medical practice and knowledge.

Acute cerebral ischemia is caused by a reduction of blood flow in the brain. This leads more or less to brain dysfunctions and damage and neuronal death. The extent of brain injury mainly depends on the level and duration of ischemia. The physiological processes involved in ischemia-induced neuronal death are complex. Briefly, the reduction in cerebral blood flow compromises tissue energy stores and leads to a deficit in oxygen and glucose. At the cellular level, a critical consequence of this metabolic deprivation is an increase of the intracellular sodium concentration. This leads to an exaggerated efflux and uptake failure of many neurotransmitters, among them is glutamate (Dirnagl et al., Trends Neurosci. 22: 391, 1999). The excessive release of glutamate over-activates N-methyl-D-aspartate (NMDA) receptors. This results in a NMDA receptor-mediated neuronal depolarization and intra-neuronal calcium influx that overstep the physiological bounds and lead to neuronal death through necrotic and apoptotic mechanisms (Choi et al., J. Neurosci., 8: 185, 1988; Sattler et al., J. Neurochem., 71: 2349, 1998). Therefore, two strategies have been pursued for the treatment of ischemic stroke: a limitation of the vascular insult by early reperfusion and/or a blockade of the neurotoxic cascade initiated by glutamate.

Today, early reperfusion by rt-PA-induced thrombolysis is the only treatment of stroke approved by the Food and Drug Administration and the European Medical Agencies. However, as stated above, despite its beneficial effects, thrombolytic therapy is associated with a risk of hemorrhagic transformation and neuronal death potentiation (Tsirka et al., Nature, 377: 340-344, 1995; Wang et al., Nature Med., 4: 228-231, 1998; Kaur et al., J. Cereb. Blood Flow Metab. 24: 945, 2004).

In contrast, the use of NMDA glutamate receptor antagonists yet has not been proven being efficient in humans, because prototypical (high-affinity) NMDA receptor antagonists possess an intrinsic behavioral toxicity, which is believed to be related to the occurrence of vacuolizations in neurons of the posterior cingulated and retro-splenial cortices (Olney et al., Science, 244:1360, 1989; 254: 1515, 1991; Davis et al., Stroke, 31:347, 2000). In order to resolve this problem, the development and the use of low-affinity (atypical) NMDA receptor antagonists is now considered as a major therapeutic strategy (Parsons et al., Drug News Perspect. 11: 523, 1998; Smith, Curr. Opin. Investig. Drugs, 4:826, 2003).

Interestingly, the anesthetic gases xenon and nitrous oxide possess a pharmacological profile that resembles that of the low-affinity NMDA receptor, with antagonistic properties at both the NMDA receptor and the nicotinic cholinergic receptor (Franks et al., Nature 396: 324, 1998; Jevtovic et al., Nature Med. 4: 460, 1998; Yamakura and Harris, Anesthesiology 93: 1095, 2000; David et al., Biol. Psychiatry, 60:49, 2006), and further exhibit neuroprotective properties against ischemia with no proven adverse side effects when used at non-anesthetic concentrations (David et al., J. Cereb. Blood Flow Metab., 23:1168, 2003; FASEB J., 22:1275, 2008; Homi et al., Anesthesiology, 99:876, 2003; Ma et al., Ann. Neurol., 58:182, 2005; Martin et al., Br. J. Anaesth., 98:236, 2007; Rajakumaraswamy et al., Neurosci. Lett., 409:128, 2006; Haelewyn et al., Crit. Care Med., in press). In addition, uniquely among the few molecules that show low-affinity antagonistic activity at the NMDA glutamatergic receptor, xenon and nitrous oxide readily cross the blood-brain barrier and have low blood/gas solubility that is advantageous in terms of rapid inflow and wash-out (Goto et al., Br. J. Anaesth, 880:255, 1998), conditions that may favor treatment and reduce the risk of adverse side effects such as the occurrence of behavioral toxicity. Argon, helium, and neon have also been shown to be cardioprotective and/or neuroprotective (Yarin et al., Hear Res., 201:1, 2005; Pan et al., Exp Neurol., 205:587, 2007; Pagel et al., Anesth Analg., 105:562, 2007). Thus, some neuroprotective properties of nitrous oxide, xenon and argon have been patented. See for instance U.S. Pat. Nos. 6,274,633 and 6,653,354, which relate to the use of xenon as an NMDA antagonist, in particular for providing neuroprotection, or European patent EP 1 158 992, which teaches the use of xenon or of a mixture of xenon and oxygen, nitrogen or air, to treat neurointoxications. See also French patent FR 2 863 169, which relates to the use of argon or of gas mixtures containing argon for treating neurointoxications.

Taken together, these data have led to the conclusion that methods of treatment of ischemic insults comprising more than one therapeutic approaches are now needed to provide both blood flow reperfusion and efficient neuroprotection, and further reduce or inhibit undesirable damaging host responses such as the risk of hemorrhaging transformation and neuronal death potentiation associated with thrombolytic therapy (Yanaka et al., Drugs Today, 36:12, 2000; Kaur et al., J. Cereb. Blood Flow Metab. 24: 945, 2004); of course, all therapeutic approaches should not oppose each other's benefits.

Surprisingly, the inventors discovered that the neuroprotective gases nitrous oxide, argon, xenon, helium, neon, and mixtures thereof, when administered at specific concentration ranges, can inhibit directly the catalytic activity of serine proteases, such as t-PA and plasmin, and thereby reduce the beneficial properties as well as adverse side effects that are associated with thrombolytic drugs and therapy.

Thus, when administered at appropriate concentrations, gases selected from the group consisting of nitrous oxide, xenon, argon, helium, neon, and mixtures thereof, can be advantageously used for providing efficient (unaltered) thrombolysis and reducing the risk of hemorrhagic transformation and neuronal death potentiation that is associated with thrombolytic drugs and therapy in the treatment of ischemia. Thus, these gases and mixtures thereof can thus be used both for providing neuroprotection and for inhibiting the adverse effects of the proteolytic (catalytic) properties of serine proteases, especially in the treatment of ischemia, in humans or animals, i.e. in human and veterinary medicine.

The present invention thus relates to a pharmaceutical composition comprising: (i) at least one thrombolytic drug (A) acting through the plasminogen activator-plasmin system, such as the human recombinant form of tissue-type plasminogen activator (rt-PA), and (ii) at least one gas (B) selected from the group consisting of the neuroprotective gases nitrous oxide, argon, xenon, helium, neon, and mixtures thereof, as a combined composition for simultaneous, separate or sequential use for treating ischemic insults, such as cerebral ischemia, cardiac ischemia, renal ischemia, retinal ischemia, or lower limb's ischemia or any other type of ischemia that can affect the mammals' body, especially the humans' body.

Agent (A) is typically a serine protease possessing thrombolytic properties, such as, but not limited to, the recombinant tissue-type plasminogen activator (rt-PA) also called alteplase, streptokinase, urokinase, reteplase or tenecteplase.

Advantageously, agent (A), such as rt-PA, is intended for intravenous or intra-arterial injection or any other appropriate route of administration.

Advantageously, said at least one gas (B) is intended for inhalable administration or any other appropriate route of administration.

According to a first advantageous embodiment of the invention, agent (A) is administered alone, or with agent (B) consisting of at least one gas or a mixture of gases selected from the neuroprotective gases nitrous oxide, xenon, argon, helium, and neon, wherein said at least one gas (B) is at concentrations that do not reduce or delay agent (A)-induced thrombolysis due to the risk of inhibiting the benefits of thrombolysis therapy since those gases were found to inhibit the catalytic and thrombolytic properties of t-PA (ethical principle of caution). Said at least one gas (B) can be administered before and/or during the administration of agent (A).

According to a particular embodiment of the invention, the pharmaceutical composition of the present invention comprises only one gas selected from nitrous oxide, xenon, argon, helium, and neon.

Particularly advantageously according to the present invention, agent (B) is xenon in a volume proportion between 1% and 40%, more advantageously between 1% and 35%, more advantageously between 10% and 35%, most advantageously between 15% and 25%.

Or, particularly advantageously according to the present invention, agent (B) is nitrous oxide in a volume proportion between 1% and 40%, more advantageously between 1% and 35%, more advantageously between 15% and 35%, most advantageously between 20% and 30%.

Or, particularly advantageously according to the present invention, agent (B) is helium in a volume proportion between 1% and 40%, more advantageously between 1% and 35%, more advantageously between 15 and 35%, most advantageously between 25% and 30%.

Or, particularly advantageously according to the present invention, agent (B) is neon in a volume proportion between 1% and 40%, more advantageously between 1% and 35%, more advantageously between 15 and 35%, most advantageously between 25% and 30%.

Or, particularly advantageously according to the present invention, agent (B) is argon in a volume proportion between 46% and 99%, more advantageously between 50% and 80%, most advantageously between 50% and 75%.

According to another particular embodiment of the invention, the pharmaceutical composition of the present invention comprises a mixture of gases selected from nitrous oxide, xenon, argon, helium, and neon. Preferably, it comprises a mixture of two gases selected from nitrous oxide, xenon, argon, helium, and neon. Gases are in equimolar or non-equimolar volume proportions.

Particularly advantageously according to the present invention, agent (B) is a mixture of xenon and nitrous oxide, the volume proportion of xenon being between 1% and 40%, more advantageously between 5% and 20%, most advantageously between 5% and 10%, and the volume proportion of nitrous oxide being between 1% and 40%, more advantageously between 5% and 20%, most advantageously between 5% and 10%.

Or, particularly advantageously according to the present invention, agent (B) is a mixture of xenon and helium, the volume proportion of xenon being between 1% and 40%, more advantageously between 5% and 20%, most advantageously between 5% and 10%, and the volume proportion of helium being between 1% and 40%, more advantageously between 5% and 20%, most advantageously between 5% and 10%.

Or, particularly advantageously according to the present invention, agent (B) is a mixture of xenon and argon, the volume proportion of xenon being between 1% and 50%, more advantageously between 5% and 25%, most advantageously between 10% and 15%, and the volume proportion of argon being between 1% and 25%, more advantageously between 5% and 25%, most advantageously between 10% and 15%.

Or, particularly advantageously according to the present invention, agent (B) is a mixture of nitrous oxide and argon, the volume proportion of nitrous oxide being between 1% and 40%, more advantageously between 5% and 20%, most advantageously between 5% and 10%, and the volume proportion of argon being between 1% and 40%, more advantageously between 5% and 20%, most advantageously between 5% and 10%.

Or, particularly advantageously according to the present invention, agent (B) is a mixture of nitrous oxide and helium, the volume proportion of nitrous oxide being between 1% and 40%, more advantageously between 5% and 20%, most advantageously between 5% and 10%, and the volume proportion of helium being between 1% and 40%, more advantageously between 5% and 20%, most advantageously between 5% and 10%.

Or, particularly advantageously according to the present invention, agent (B) is a mixture of helium and argon, the volume proportion of helium being between 1% and 50%, more advantageously between 5% and 30%, most advantageously between 10% and 20%, and the volume proportion of argon being between 1% and 50%, more advantageously between 5% and 30%, most advantageously between 10% and 20%.

Or, particularly advantageously according to the present invention, agent (B) is a mixture of xenon and neon, the volume proportion of xenon being between 1% and 40%, more advantageously between 5% and 20%, most advantageously between 5% and 10%, and the volume proportion of neon being between 1% and 40%, more advantageously between 5% and 20%, most advantageously between 5% and 10%.

Or, particularly advantageously according to the present invention, agent (B) is a mixture of nitrous oxide and neon, the volume proportion of nitrous oxide being between 1% and 40%, more advantageously between 5% and 20%, most advantageously between 5% and 10%, and the volume proportion of neon being between 1% and 40%, more advantageously between 5% and 20%, most advantageously between 5% and 10%.

Or, particularly advantageously according to the present invention, agent (B) is a mixture of neon and argon, the volume proportion of neon being between 1% and 50%, more advantageously between 5% and 30%, most advantageously between 10% and 20%, and the volume proportion of argon being between 1% and 50%, more advantageously between 5% and 30%, most advantageously between 10% and 20%.

Advantageously according to the present invention, for all the volume proportions of gases indicated above, the remainder of gases is either oxygen alone or oxygen completed with nitrogen. Most advantageously according to the present invention, the remainder of gases is oxygen alone, since oxygen was found to enhance the thrombolytic properties of t-PA and thereby to favor blood flow reperfusion.

According to a second advantageous embodiment of the invention, agent (A) is administered together with 100 vol % oxygen, since oxygen was found to enhance the thrombolytic properties of t-PA and thereby to favor blood flow reperfusion.

According to a third advantageous embodiment of the invention, once blood flow has been restored by agent (A), agent (B) selected from the group consisting of nitrous oxide, argon, xenon, helium, neon, and mixtures thereof, can be administered at the same concentration as before, or, if necessary, can be given at higher concentrations that reduce the catalytic activity of agent (A), in order to reduce the risk of hemorrhagic transformation and neuronal death potentiation associated with agent (A)-induced thrombolysis and therapy.

According to a particular embodiment of the invention, the pharmaceutical composition of the present invention comprises only one gas selected from nitrous oxide, xenon, argon, helium, and neon.

Particularly advantageously according to the present invention, agent (B) is xenon in a volume proportion between 30% and 99%, more advantageously between 36% and 99%, more advantageously between 40% and 80%, most advantageously between 35% and 50%.

Or, particularly advantageously according to the present invention, agent (B) is nitrous oxide in a volume proportion between 30% and 99%, more advantageously between 36% and 99%, more advantageously between 40% and 80%, most advantageously between 35% and 50%.

Or, particularly advantageously according to the present invention, agent (B) is helium in a volume proportion between 30% and 99%, more advantageously between 36% and 99%, more advantageously between 50 and 80%, most advantageously between 50% and 75%.

Or, particularly advantageously according to the present invention, agent (B) is neon in a volume proportion between 30% and 99%, more advantageously between 36% and 99%, more advantageously between 50 and 80%, most advantageously between 50% and 75%.

Or, particularly advantageously according to the present invention, agent (B) is argon in a volume proportion between 1% and 45%, more advantageously between 10% and 40%, more advantageously between 15% and 40%, most advantageously between 25% and 35%.

According to another particular embodiment of the invention, the pharmaceutical composition of the present invention comprises a mixture of gases selected from nitrous oxide, xenon, argon, helium, and neon. Preferably, it comprises a mixture of two gases selected from nitrous oxide, xenon, argon, helium, and neon.

Particularly advantageously according to the present invention, agent (B) is a mixture of xenon and nitrous oxide, the volume proportion of xenon being between 1% and 80%, more advantageously between 10% and 40%, most advantageously between 15% and 35%, and the volume proportion of nitrous oxide being between 1% and 80%, more advantageously between 10% and 40%, most advantageously between 15% and 35%.

Or, particularly advantageously according to the present invention, agent (B) is a mixture of xenon and helium, the volume proportion of xenon being between 1% and 80%, more advantageously between 10% and 40%, most advantageously between 15% and 35%, and the volume proportion of helium being between 1% and 80%, more advantageously between 10% and 40%, most advantageously between 15% and 35%.

Or, particularly advantageously according to the present invention, agent (B) is a mixture of xenon and argon, the volume proportion of xenon being between 1% and 80%, more advantageously between 10% and 40%, most advantageously between 20% and 35%, and the volume proportion of argon being between 1% and 80%, more advantageously between 10% and 40%, most advantageously between 20% and 35%.

Or, particularly advantageously according to the present invention, agent (B) is a mixture of nitrous oxide and argon, the volume proportion of nitrous oxide being between 1% and 80%, more advantageously between 10% and 40%, most advantageously between 15% and 35%, and the volume proportion of argon being between 1% and 80%, more advantageously between 10% and 40%, most advantageously between 15% and 35%.

Or, particularly advantageously according to the present invention, agent (B) is a mixture of nitrous oxide and helium, the volume proportion of nitrous oxide being between 1% and 80%, more advantageously between 10% and 40%, most advantageously between 15% and 35%, and the volume proportion of helium being between 1% and 80%, more advantageously between 10% and 40%, most advantageously between 15% and 35%.

Or, particularly advantageously according to the present invention, agent (B) is a mixture of helium and argon, the volume proportion of helium being between 1% and 80%, more advantageously between 10% and 40%, most advantageously between 15% and 35%, and the volume proportion of argon being between 1% and 80%, more advantageously between 10% and 40%, most advantageously between 15% and 35%.

Or, particularly advantageously according to the present invention, agent (B) is a mixture of xenon and neon, the volume proportion of xenon being between 1% and 80%, more advantageously between 10% and 40%, most advantageously between 15% and 35%, and the volume proportion of neon being between 1% and 80%, more advantageously between 10% and 40%, most advantageously between 15% and 35%.

Or, particularly advantageously according to the present invention, agent (B) is a mixture of nitrous oxide and neon, the volume proportion of nitrous oxide being between 1% and 80%, more advantageously between 10% and 40%, most advantageously between 15% and 35%, and the volume proportion of neon being between 1% and 80%, more advantageously between 10% and 40%, most advantageously between 15% and 35%.

Or, particularly advantageously according to the present invention, agent (B) is a mixture of neon and argon, the volume proportion of neon being between 1% and 80%, more advantageously between 10% and 40%, most advantageously between 15% and 35%, and the volume proportion of argon being between 1% and 80%, more advantageously between 10% and 40%, most advantageously between 15% and 35%.

Advantageously according to the present invention, for all the volume proportions of gases indicated above, the remainder of gases is oxygen alone or oxygen completed with nitrogen. Particularly advantageously, the volume proportion of oxygen is less than 30% in order to avoid the deleterious oxygen-induced production of free radicals (Asahi et al., J. Cereb. Blood Flow Metab. 20: 452, 2000) and possible oxygen-induced facilitation of the risk of hemorrhagic transformation and neuronal death potentiation associated with t-PA therapy, since oxygen was found to increase the catalytic activity of rt-PA (ethical principle of caution). Typically, the volume proportion of oxygen is comprised between 19 vol % and 30 vol %, more advantageously between 21 vol % and 25 vol %.

Also advantageously according to the present invention, said agent (B) consisting in at least one gas or a mixture of gases selected from the neuroprotective gases nitrous oxide, xenon, argon, helium, and neon at concentrations that reduce the catalytic activity of thrombolytic drugs, such as rt-PA, is administered to the patient with an appropriate delay in order not to favor re-occlusion since those gases were found to inhibit the thrombolytic properties of rt-PA (ethical principle of caution). Advantageously, since re-occlusion has been shown to occur in 10-15% of patients 41±43 min after rt-PA-induced reperfusion (Rubiera et al., Stroke, 36: 1452, 2005), said at least one gas (B) is administered with a delay comprised between 5 and 180 min (3 h) after administration of agent (A), more advantageously with a delay of 60 to 180 min, most advantageously with a delay comprised between 120 and 180 min, after administration of agent (A).

According to a fourth advantageous embodiment of the invention, said agent (B) consisting in at least one gas or a mixture of gases selected from the neuroprotective gases nitrous oxide, xenon, argon, helium and neon is administered simultaneously, separately or sequentially with other drugs and/or any particular conditions, which can enhance the neuroprotective action of said at least one gas (B). Such drugs can be for instance alpha(2)-adrenoceptor agonists, such as Dexmedetomidine (Rajakumaraswamy et al., Neurosci Lett. 409:128, 2006), carbon monoxide, nitric oxide, and/or hydrogen which is a non inert gas shown to possess therapeutic antioxidant properties (Osawa et al., Nature Med. 13:688, 2007). Typically, carbon monoxide or nitric oxide is administered at concentrations of a few ppm. Typically, hydrogen is administered in a volume proportion of 0.5 to 4.7%. Such particular conditions are for instance hypothermia (Ma et al., Ann Neurol., 58:182, 2005; Hobbs et al., Stroke, 39:1307, 2008).

Advantageously according to the present invention, agent (A), such as rt-PA, is first administered to the patient in order to restore blood flow, advantageously within an appropriate therapeutic window following the occurrence of the symptoms of ischemia. Advantageously, agent (A) is administered together with 100 vol % oxygen, or with agent (B) consisting of at least one gas or a mixture of gases selected from the neuroprotective gases nitrous oxide, xenon, argon, helium, and neon, wherein said at least one gas (B) is at concentrations that do not reduce or delay agent (A)-induced thrombolysis. Then, once blood flow has been restored, agent (B) selected from the group consisting of nitrous oxide, argon, xenon, helium, neon, and mixtures thereof, can be administered at the same concentration as before, or, if necessary, can be given at higher concentrations that reduce the catalytic activity of agent (A).

According to another advantageous embodiment, the pharmaceutical composition of the present invention is intended for inhalable administration, such as oral inhalation or nasal inhalation, or any other appropriate route of administration. If inhaled, the pharmaceutical composition according to the invention is administered to the patient via his upper respiratory pathways, i.e. by inhalation via the nose and/or the mouth, using any suitable administration device comprising a patient respiratory interface, such as a respiratory mask or a tracheal probe, one or more feed pipes serving to convey the gaseous pharmaceutical composition from a source containing the said pharmaceutical composition to the interface, and a regulator and/or a medical or an anesthesia ventilator serving to deliver and/or extract the patient's respiratory gas.

The present invention also relates to the use of at least one thrombolytic agent (A), such as the human recombinant form of tissue-type plasminogen activator (rt-PA), and at least one gas (B) selected from the group consisting of nitrous oxide, argon, xenon, helium, neon, and mixtures thereof, for the preparation of a combined pharmaceutical composition for treating ischemic insults.

The present invention also relates to a method for limiting the risk of hemorrhagic transformation and/or neuronal death enhancement associated with rt-PA therapy or an analogous thrombolytic therapy in the treatment of a patient afflicted with ischemia, said method comprising administering to the patient an effective amount of at least one gas (B) selected from the group consisting of nitrous oxide, argon, xenon, helium, neon, and mixtures thereof, as described above.

The present invention also relates to a method for treating ischemia in a patient, while limiting the risk of hemorrhagic transformation and/or neuronal death enhancement, which comprises administering to said patient:
a thrombolytic agent (A), advantageously with oxygen and at least one gas (B) selected from the group consisting of nitrous oxide, argon, xenon, helium, neon, and mixtures thereof, as a combined composition for separate and sequential use.

The following figures and examples describe and illustrate the present invention, but do not restrict the present invention.

FIGS. 1A to 1C shows the inhibiting effect of various concentrations of nitrous oxide (FIG. 1A), xenon (FIG. 1B), and helium (FIG. 1C) on the catalytic activity of t-PA.

FIG. 1D shows the effects of xenon, argon, and helium at 75 vol % on the catalytic activity of plasmin.

FIG. 1E shows the effects of various gas mixtures containing xenon, nitrous oxide, helium, and/or argon at various concentrations on the catalytic activity of t-PA.

FIG. 5A shows the neuroprotective effect of nitrous oxide on neuronal death induced by an intracerebral injection of NMDA.

FIG. 5B shows the t-PA-induced increase of neuronal death induced by an intracerebral injection of NMDA.

FIG. 5C shows the reduction by nitrous oxide of the t-PA-induced increase of neuronal death induced by an intracerebral injection of NMDA.

EXAMPLES

All animal-use procedures were in accordance with the guidelines of the National Institute of Health (USA) and The European Communities Council Directive of 24 Nov. 1986 (86/609/EEC) for the care and use of laboratory animals, and were further agreed by our local ethic committee. The inventor was fully authorized (agreement no. 14-27).

Example 1

Figure 1:
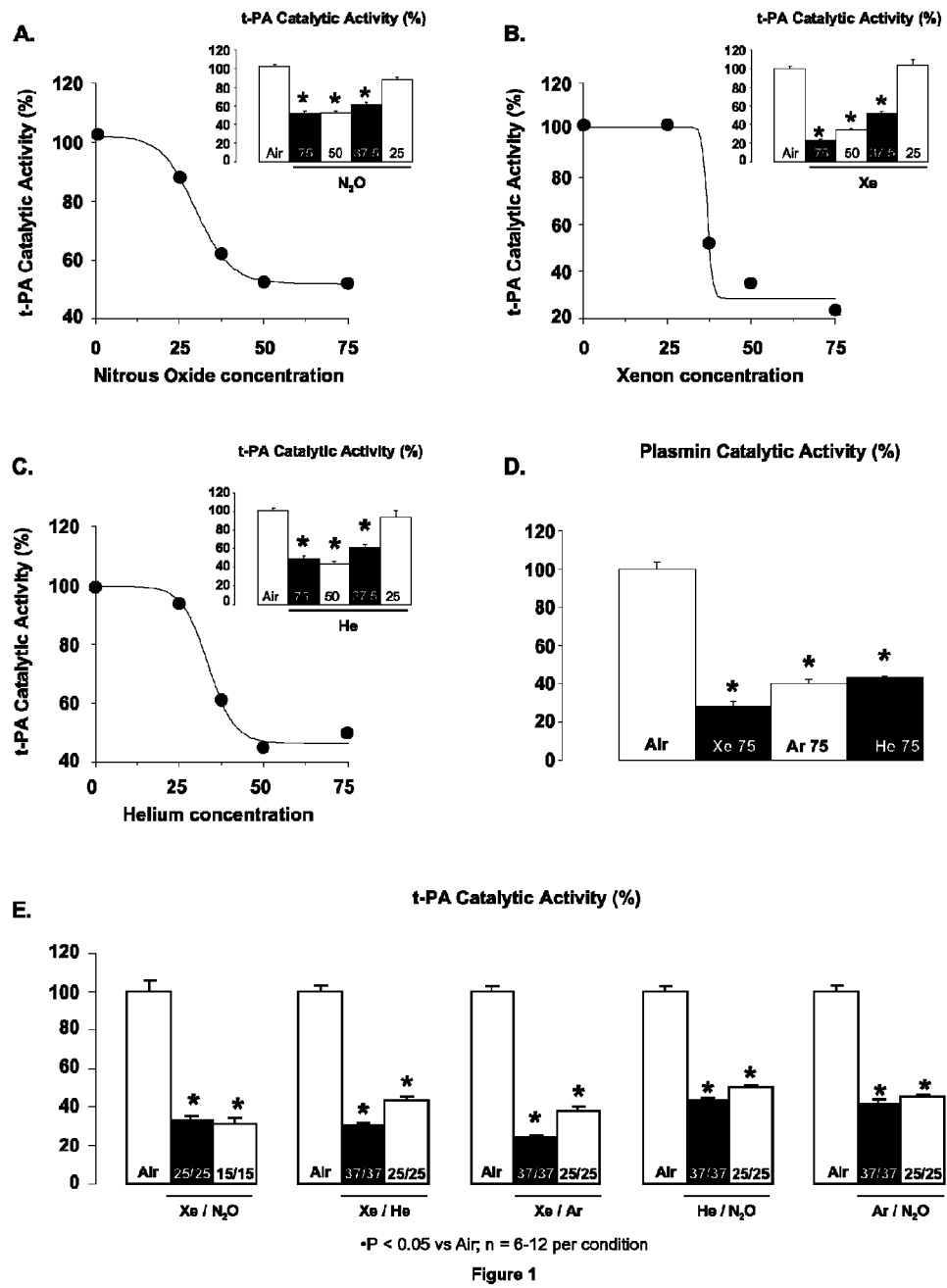
FIG. 1 illustrates the inhibiting effect of various concentrations of gases selected from nitrous oxide, xenon, helium, and argon on the catalytic activity of t-PA, the serine protease that constitutes the only authorized therapy for treating ischemic diseases.

Effect of Various Concentrations of Nitrous Oxide, Xenon, Argon, and Helium on the Catalytic Activity of t-Pa and Plasmin Ex Vivo (FIG. 1)

All experiments were performed as follows: Fifty (50) μL of human recombinant t-PA was incubated with 50 μL of its substrate: methylsulfonyl-D-phenyl-glycil-arginine-7-amino-4-methylcoumarin acetate. For plasmin, twenty five (25) μL of human recombinant plasmin was incubated with 25 μL of its substrate: H-D-norleucyl-hexahydrotyrosol-lysine-para-nitroanilide diacetate. The kinetics of the catalytic activity of t-PA or plasmin was immediately measured using a spectrophotometer, and then estimated using the initial rate method. Solutions of t-PA or plasmin and their substrates were saturated with air (control), or with nitrous oxide, argon, xenon, or helium at concentrations of 15 vol % to 75 vol %, the remainder being oxygen at 25 vol %, completed with nitrogen when necessary.

FIGS. 1A to 1C shows the inhibiting effect of various concentrations of nitrous oxide (FIG. 1A), xenon (FIG. 1B), and helium (FIG. 1C) on the catalytic activity oft-PA. FIG. 1D shows the effects of xenon, argon, and helium at 75 vol % on the catalytic activity of plasmin. FIG. 1E shows the effects of various gas mixtures containing xenon, nitroux oxide, helium, and/or argon at various concentrations on the catalytic activity of t-PA.

For all gas mixtures in FIG. 1, the remainder is 25 vol % oxygen completed with nitrogen if necessary.

It can be concluded that the catalytic activity of t-PA is reduced by one gas or a mixture of gases selected from nitrous oxide, xenon, argon, and helium, thereby showing that these gases are serine protease inhibitors.

Example 2

Figure 2:
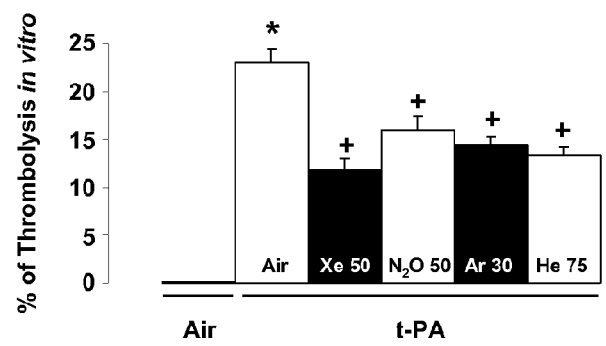
FIG. 2 illustrates the inhibiting effect of xenon, nitrous oxide, argon, and helium on the thrombolytic action of t-PA in vitro.
Figure 3:
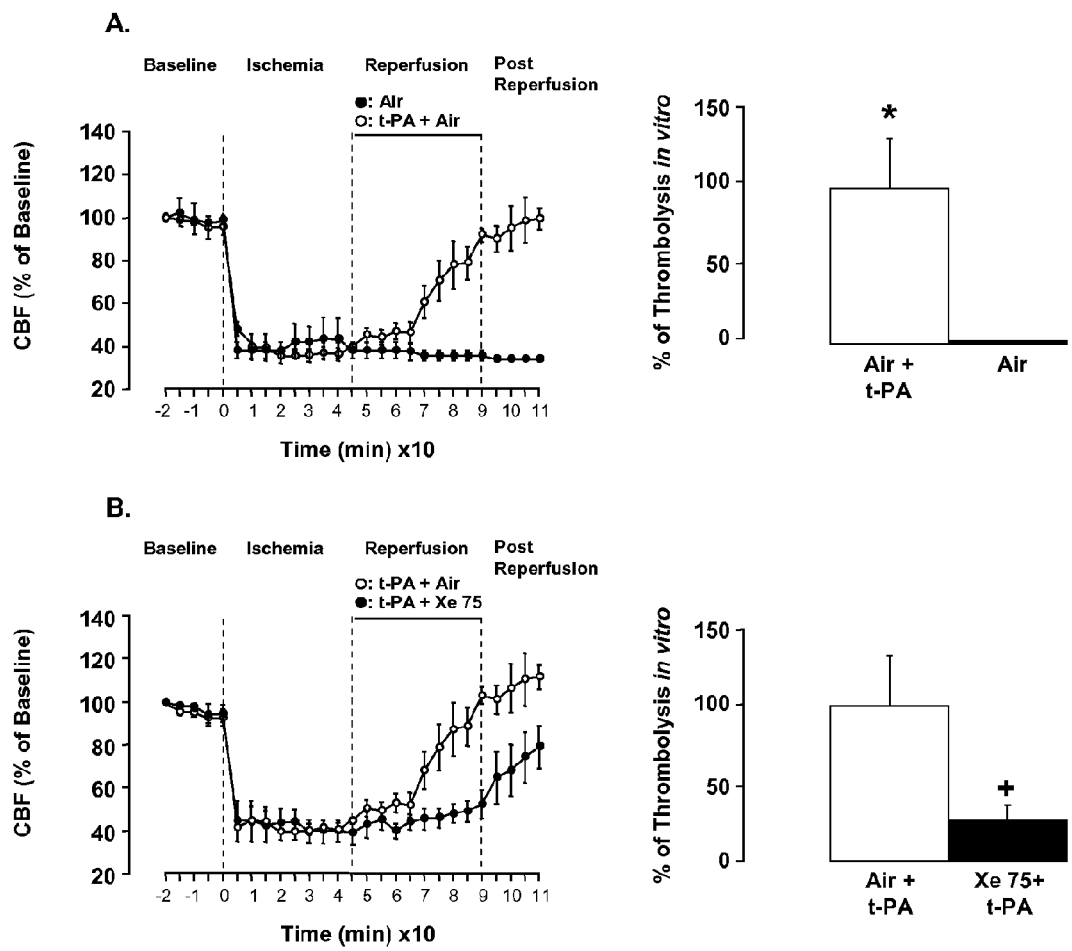
FIG. 3 illustrates the thrombolytic effect of t-PA alone (FIG. 3A) and the inhibiting effect of xenon on the thrombolytic action of t-PA (FIG. 3B) in vivo in rats subjected to middle cerebral artery occlusion using an autologous blood clot.

Effects of Nitrous Oxide, Xenon, Argon, and Helium on the Thrombolytic Action of t-PA Ex Vivo and In Vivo (FIGS. 2 and 3)

In vitro experiments (FIG. 2) were performed using Male adult Sprague-Dawley rats (500±50 g). The rats were killed by decapitation. A volume of 500 μL of rat blood was transferred in different pre-weighed sterile Eppenforf™ tubes of 1.5 mL volume and incubated at 37° C. for 15 hours.

After clot formation, serum was completely removed, aspired out without disturbing the clot formed, and each tube was again weighed to determine the clot weight (clot weight=weight of tube containing clot−weight of tube alone). Each tube containing clot was properly labeled and filled with 1 mL of a saline solution containing 0.008 mg/mL of t-PA, saturated beforehand with medical air (control), nitrous oxide, xenon, argon or a mixture of nitrous oxide and argon. Some tubes were filled with saline alone saturated with medical air to serve as a negative control. All tubes were then incubated at 37° C. for 1 h 30 min. After incubation, the fluid obtained was removed and tubes were again weighed to observe the difference in weight after clot disruption. Difference obtained in weight taken before and after clot lysis was expressed as a percentage of clot lysis.

As shown in FIG. 2, when given alone, t-PA saturated with medical air (control) induces clot lysis (around 23% of clot lysis). Xenon at 50 vol %, nitrous oxide at 50 vol %, argon at 30 vol %, and helium at 75 vol % reduce t-PA-induced clot lysis.

In vivo experiments (FIG. 3) were performed in Male adult Sprague-Dawley rats (290±40 g). The animals had free access to food and water in an animal room at constant temperature and humidity. Rats monitored for their physiological functions were anesthesized, and subjected to cerebral ischemia by occlusion of the middle cerebral artery using an autologus blood clot obtained from whole blood withdrawn from the rat 24 h prior surgery, allowed to clot at 37° C. for 2 h, and then and stored at 4° C. for 22 h.

Embolic occlusion of the middle cerebral artery was induced using an autologous blood clot. Briefly, a blood clot of 4 cm long was injected with a volume of 504 of saline into the middle cerebral artery. Forty-five minutes after occlusion of the middle cerebral artery, the rats were given t-PA intravenously (0.9 mg/kg; 10% bolus, 90% perfusion during 45 minutes) in order to induce thrombolysis. Five minutes before the bolus injection and all along the perfusion period with t-PA, the rats were treated with medical air (controls) or xenon. Then, the catheter was removed, and all the incisions closed. After the experiment, the rats were allowed moving freely in their home cage with free access to food and water.

As shown in FIG. 3, while rats not treated with t-PA show no reperfusion, those treated with t-PA exhibit reperfusion as the consequence of blood clot thrombolysis (FIG. 3A). In agreement with the in vitro studies above, rats treated with t-PA and xenon at 75 vol % (FIG. 3B) exhibit a lower reperfusion rate than control rats treated with t-PA and medical air.

It can be concluded from these in vitro and in vivo experiments that t-PA-induced thrombolysis is reduced by one gas selected from nitrous oxide, xenon, argon, and helium.

Example 3

Figure 4:
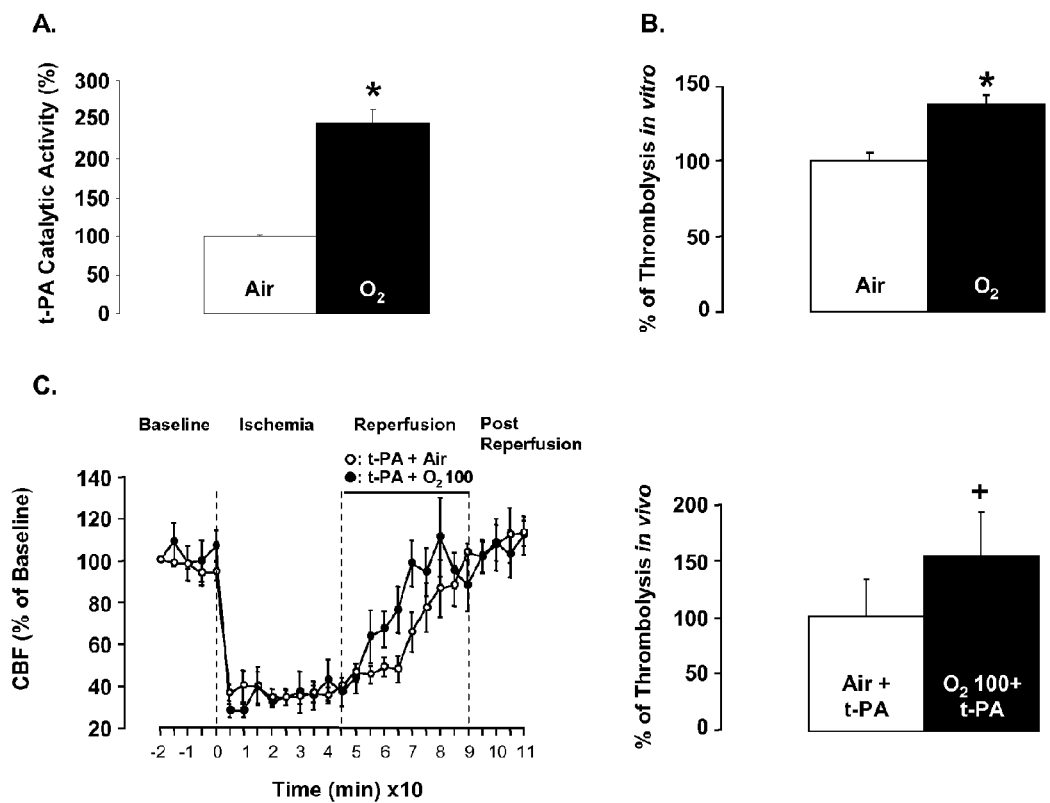
FIG. 4 shows the effect of oxygen on the catalytic activity of t-PA (FIG. 4A), and its thrombolytic action in vitro (FIG. 4B), and in vivo in rats subjected to middle cerebral artery occlusion using an autologous blood clot (FIG. 4C).

Effects of Oxygen on the Catalytic Activity and Thrombolytic Properties of t-PA (FIG. 4)

The effects of oxygen on the catalytic activity and thrombolytic properties of t-PA were also evaluated in vitro and in vivo according to the methods described above.

FIG. 4 shows the effect of oxygen on the catalytic activity, the in vitro thrombolytic action, and the in vivo thrombolytic properties of t-PA in rats subjected to middle cerebral artery occlusion using an autologous blood clot. Oxygen at 100 vol % increases the catalytic activity (FIG. 4A), and facilitates the in vitro (FIG. 4B) and in vivo (FIG. 4C) thrombolytic action of t-PA.

It can be concluded that the catalytic activity and the thrombolytic properties of t-PA are enhanced by oxygen.

Example 4

Figure 5:
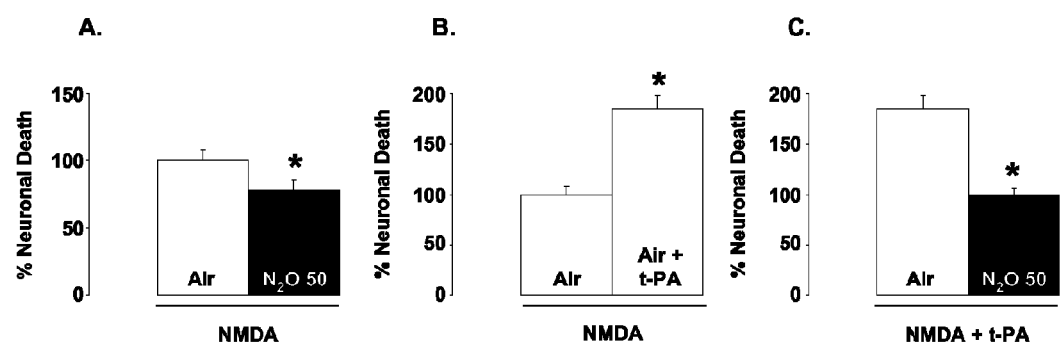
FIG. 5 illustrates the inhibiting effect of nitrous oxide on the risk of neuronal death enhancement associated with t-PA therapy in vivo.

Effects of Nitrous Oxide on NMDA-Induced Neuronal Death in the Absence or the Presence of t-PA (FIG. 5)

Experiments were conducted in Male adult Sprague-Dawley rats. The rats were given, under short halothane-oxygen anesthesia of 10 min duration, an intracerebral injection of 50 nmol NMDA, alone or in combination with 3 mg t-PA, in 1 mL saline solution.

One hour later, the rats were treated for a 3 h period in an environmental chamber saturated with nitrous oxide at 50 vol % with the remainder being oxygen at 25 vol % completed with nitrogen.

Forty-eight (48) hours after NMDA injection, rats were killed by decapitation under halothane-oxygen anesthesia. The brain was rapidly removed, frozen in isopentane, placed at −80° C. Coronal brain sections (20 μm) were then cryostat-cut, mounted on gelatinized slides, and stained with thionin. Brain sections colored with thionin were then digitized on a PC computer, and analyzed with an image analyzer (ImageJ® software, Scion corp., USA) by two blinded scientists. Values were averaged; value differences were no more than 10% (mean: 0.5±1%). The lesion areas were delineated by the pallor of histological staining in the necrotic tissue compared with the surrounding healthy tissue. The infarction volume was calculated by integration over the whole brain of the infarcted surfaces, using the sterotaxic atlas for the rat brain of Paxinos and Watson (Academic Press, 1998).

For instance, nitrous oxide at 50 vol % reduces neuronal death produced by NMDA by 22% (FIG. 5A).

Co-administration of t-PA with 50 nmol NMDA increases NMDA-induced neuronal death (FIG. 5B). Nitrous oxide at 50 vol % reduces neuronal death induced by co-administration of t-PA and NMDA by 45% (FIG. 5C), i.e. in a greater manner that it reduces neuronal death induced by NMDA alone. This indicates that nitrous oxide at 50 vol % reduces the proteolytic action of t-PA responsible for the enhancement of neuronal death after t-PA therapy by approximately 23% (45%−22%=23%).

It can be concluded that the adverse side effects associated with t-PA therapy responsible for the risk of hemorrhagic transformation and neuronal death enhancement are reduced by nitrous oxide.

The invention claimed is:

1. A method of treating ischemic insults, comprising administering to a human or animal in need thereof at least one thrombolytic agent (A) and at least one gas (B) selected from the group consisting of nitrous oxide, argon, xenon, helium, neon, and mixtures thereof, wherein said agent (A) is first administered to the patient in order to restore blood flow and then said gas (B) is administered once blood flow has been restored, wherein said gas (B) is at concentrations that reduce the catalytic activity of said agent (A).

2. The method as claimed in claim 1, wherein said gas (B) is administered before, together with, and/or after at least one other drug and/or any particular condition that can enhance the reduction of the catalytic activity of said agent (A) produced by said gas (B).

3. The method as claimed in claim 1, wherein said gas (B) is xenon, nitrous oxide, helium, or neon, in a volume proportion between 36% and 99%.

4. The method as claimed in claim 1, wherein said gas (B) is argon in a volume proportion between 1% and 45%.

5. The method as claimed in claim 1, further comprising an initial administration of gas (B) prior to said administration of gas (B) once blood flow has been restored, wherein said gas (B) in said initial administration is administered before or together with said first administration of said agent (A), and wherein said gas (B) in said initial administration is at concentrations that do not reduce or delay agent (A)-induced thrombolysis.

6. The method as claimed in claim 5, wherein said gas (B) in said initial administration is xenon, nitrous oxide, helium, or neon, in a volume proportion between 1% and 35%.

7. The method as claimed in claim 5, wherein said gas (B) in said initial administration is argon in a volume proportion between 46% and 99%.

8. The method as claimed in claim 5, wherein said gas (B) in said initial administration is selected from the group consisting of a mixture of xenon and nitrous oxide, the volume proportion of xenon and of nitrous oxide being each between 1% and 40%; a mixture of xenon and helium, the volume proportion of xenon and of helium being each between 1% and 40%; a mixture of nitrous oxide and argon, the volume proportion of nitrous oxide and of argon being each between 1% and 40%; a mixture of nitrous oxide and helium, the volume proportion of nitrous oxide and of helium being each between 1% and 40%; a mixture of argon and helium, the volume proportion of argon and of helium being each between 1% and 50%; and a mixture of xenon and argon, the volume proportion of xenon being between 1% and 50% and the volume proportion of argon being between 1% and 25%.

9. The method as claimed in claim 1, wherein the remainder of gases is either oxygen alone or oxygen completed with nitrogen.

10. The method as claimed in claim 1, wherein said gas (B) is selected from the group consisting of a mixture of xenon and nitrous oxide, the volume proportion of xenon and of nitrous oxide being each between 1% and 80%; a mixture of xenon and helium, the volume proportion of xenon and of helium being each between 1% and 80%; a mixture of nitrous oxide and argon, the volume proportion of nitrous oxide and of argon being each between 1% and 80%; a mixture of nitrous oxide and helium, the volume proportion of nitrous oxide and of helium being each between 1% and 80%; a mixture of argon and helium, the volume proportion of argon and of helium being each between 1% and 80%; and a mixture of xenon and argon, the volume proportion of xenon being between 1% and 80% and the volume proportion of argon being between 1% and 80%.

11. The method as claimed in claim 1, wherein said gas (B) is administered before, together with, and/or after at least one other drug and/or any particular condition that can enhance the neuroprotective action of said gas (B).

12. A method of treating ischemic insults as claimed in claim 1, wherein said at least one thrombolytic agent (A) is a human recombinant form of tissue-type plasminogen activator (rt-PA).

13. The method as claimed in claim 6, wherein said gas (B) in said initial administration is xenon, nitrous oxide, helium, or neon, in a volume proportion between 10% and 35%.

14. The method as claimed in claim 7, wherein said gas (B) in said initial administration is argon in a volume proportion between 50% and 80%.

15. The method as claimed in claim 3, wherein said gas (B) is xenon, nitrous oxide, helium, or neon, in a volume proportion between 40% and 80%.

16. The method as claimed in claim 4, wherein said gas (B) is argon in a volume proportion between 10% and 40%.

17. The method as claimed in claim 1, wherein the at least one thrombolytic agent (A) and the at least one gas (B) is administered to the patient from a pharmaceutical kit.

\* \* \* \* \*